United States Patent
Arnold et al.

(10) Patent No.: US 12,006,318 B2
(45) Date of Patent: Jun. 11, 2024

(54) CRYSTALLINE FORMS OF C-C CHEMOKINE RECEPTOR TYPE 4 ANTAGONIST AND USES THEREOF

(71) Applicant: RAPT THERAPEUTICS, INC., South San Francisco, CA (US)

(72) Inventors: David J. Arnold, South San Francisco, CA (US); Omar Robles, South San Francisco, CA (US); Duane E. Rudisill, South San Francisco, CA (US); David J. Wustrow, South San Francisco, CA (US); Mikhail Zibinsky, South San Francisco, CA (US); Sami Karaborni, South San Francisco, CA (US)

(73) Assignee: RAPT Therapeutics, Inc., South San Francisco, CA (US)

( * ) Notice: Subject to any disclaimer, the term of this patent is extended or adjusted under 35 U.S.C. 154(b) by 389 days.

(21) Appl. No.: 17/098,157

(22) Filed: Nov. 13, 2020

(65) Prior Publication Data
US 2021/0139487 A1 May 13, 2021

Related U.S. Application Data

(60) Provisional application No. 62/935,007, filed on Nov. 13, 2019.

(51) Int. Cl.
*C07D 487/04* (2006.01)
*A61K 9/00* (2006.01)
*A61K 9/20* (2006.01)
*A61K 9/28* (2006.01)
*C07K 16/28* (2006.01)

(52) U.S. Cl.
CPC .......... *C07D 487/04* (2013.01); *A61K 9/0053* (2013.01); *A61K 9/2018* (2013.01); *A61K 9/2054* (2013.01); *A61K 9/284* (2013.01); *C07K 16/2818* (2013.01); *C07B 2200/13* (2013.01)

(58) Field of Classification Search
CPC .................................................... C07D 487/04
See application file for complete search history.

(56) References Cited

U.S. PATENT DOCUMENTS 10,179,787 B2   1/2019 Beck et al.

FOREIGN PATENT DOCUMENTS

| WO | WO-2018/022992 A1 | 2/2018 | |
| WO | WO-2018022992 A1 * | 2/2018 | ........... A61K 31/122 |
| WO | WO-2019/090272 A1 | 5/2019 | |
| WO | WO-2021/097339 A1 | 5/2021 | |

OTHER PUBLICATIONS

Caira, M.R. (Jan. 1998). "Crystalline Polymorphism of Organic Compounds," Topics in Current Chemistry 198:163-208.
Hilfiker, R. et al. (Jan. 2006). "Relevance of Solid-state Properties for Pharmaceutical Products," Polymorphism in the Pharmaceutical Industry, 19 pages.
International Search Report dated Feb. 24, 2021, for PCT Application No. PCT/US2020/060575, filed Nov. 13, 2020, 4 pages.
Written Opinion dated Feb. 24, 2021, for PCT Application No. PCT/US2020/060575, filed Nov. 13, 2020, 7 pages.

* cited by examiner

*Primary Examiner* — John S Kenyon
(74) *Attorney, Agent, or Firm* — Irina E. Britva; Mintz, Levin, Cohn, Ferris, Glovsky and Popeo, P.C.

(57) ABSTRACT

Crystalline forms of a C-C chemokine receptor type 4 (CCR4) antagonist, oral dosage forms of same and methods of using and preparing same, are provided.

46 Claims, 4 Drawing Sheets

CRYSTALLINE FORMS OF C-C CHEMOKINE RECEPTOR TYPE 4 ANTAGONIST AND USES THEREOF

1. CROSS REFERENCES TO RELATED APPLICATIONS

This application claims priority to U.S. Application No. 62/935,007 filed Nov. 13, 2019, the disclosure of which is incorporated by reference herein in its entirety.

2. FIELD

Disclosed herein are crystalline forms of a C-C chemokine receptor type 4 (CCR4) antagonist and methods of making and using same. These compounds may be used as a therapeutic agent in the treatment of certain diseases and disorders, including, for example, cancer.

3. BACKGROUND

In general, crystalline forms of drugs are preferred over amorphous forms of drugs, in part, because of their superior stability. For example, in many situations, an amorphous drug converts to a crystalline drug form upon storage. Because amorphous and crystalline forms of a drug typically have differing physical/chemical properties, potencies and/or bioavailabilities, such interconversion is undesirable for safety reasons in pharmaceutical administration.

A key characteristic of any crystalline drug substance is the polymorphic behavior of such a material. Polymorphs are crystals of the same molecule which have different physical properties because the crystal lattice contains a different arrangement of molecules. The different physical properties exhibited by polymorphs affect important pharmaceutical parameters such as storage, stability, compressibility, density (important in formulation and product manufacturing) and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity). Solubility differences between polymorphs may, in extreme situations, result in transitions to crystalline forms that lack potency or are toxic. In addition, physical properties of a crystalline form may be important in pharmaceutical processing. For example, a particular crystalline form may form solvates more readily or may be more difficult to filter and wash free of impurities than other forms (i.e., particle shape and size distribution might be different between one crystalline form relative to other forms).

Agencies such as the United States Food and Drug Administration closely regulate the polymorphic content of the active component of a drug in solid dosage forms. In general, the regulatory agency requires batch-by-batch monitoring for polymorphic drugs if anything other than the pure, thermodynamically preferred polymorph is marketed. Accordingly, medical and commercial reasons favor synthesizing and marketing solid drugs as the thermodynamically stable polymorph, substantially free of kinetically favored polymorphs. The present application addresses these and other needs in the art.

4. SUMMARY

In one aspect, provided are crystalline forms of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol.

In one aspect, provided are crystalline forms of the benzene sulfonate salt of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol.

In one aspect, the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is provided in a form designated as form A. In one embodiment, crystalline form A has characteristic absorption peaks (2θ) at 18.4°±0.3°, 22.9°±0.3°, 21.2°±0.3°, and 15.9°±0.3° in an X-ray powder diffractogram using Cu Kα radiation. In another embodiment, the crystalline form A has characteristic absorption peaks at 12.2°±0.3°, 23.8°±0.3°, and 25.6°±0.3° in an X-ray powder diffractogram using Cu Kα radiation. In another embodiment, the crystalline form A has characteristic absorption peaks at 23.1°±0.3°, 20.0°±0.3°, and 16.2°±0.3° in an X-ray powder diffractogram using Cu Kα radiation. In another embodiment, the crystalline form A has an X-ray powder diffractogram using Cu Kα radiation as illustrated in FIG. 1. In another embodiment, the crystalline form A has a melting point of between about 170° C. and about 173° C. as determined by differential scanning calorimetry at a scan rate of 5° C./minute.

In another aspect, the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is provided in a form designated as form B. In one embodiment, crystalline form B has characteristic absorption peaks (2θ) at 18.4°±0.3°, 22.9°±0.3°, 21.2°±0.3°, and 15.9°±0.3° in an X-ray powder diffractogram using Cu Kα radiation. In another embodiment, the crystalline form B has characteristic absorption peaks at 12.2°±0.3°, 23.8°±0.3°, and 25.6°±0.3° in an X-ray powder diffractogram using Cu Kα radiation. In another embodiment, the crystalline form B has characteristic absorption peaks at 23.1°±0.3°, 20.0°±0.3°, and 16.2°±0.3° in an X-ray powder diffractogram using Cu Kα radiation. In another embodiment, the crystalline form B has an X-ray powder diffractogram using Cu Kα radiation as illustrated in FIG. 3. In another embodiment, the crystalline form B has a melting point of between about 116° C. and about 119° C. as determined by differential scanning calorimetry at a scan rate of 5° C./minute.

In another aspect, provided are pharmaceutical compositions comprising a crystalline form of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

In embodiments, the pharmaceutical compositions comprise crystalline form A and/or crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and a pharmaceutically acceptable vehicle. In embodiments, the pharmaceutical compositions comprise crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and a pharmaceutically acceptable vehicle. In embodiments, the pharmaceutical compositions comprise crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and a pharmaceutically acceptable vehicle.

In another aspect, provided are methods of using the crystalline forms of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and pharmaceutical compositions thereof to treat or prevent various diseases, such as allergy-, immune-, inflammatory-, or cancer-related diseases, disorders or conditions. Such diseases, disorders and conditions are described in detail elsewhere, as are other maladies that may be treated or prevented with the crystalline compounds described herein.

In embodiments, the disease or disorder includes an allergy-related disorder (e.g., hypersensitivity and anaphylactic responses); gastrointestinal disorders (e.g., inflammatory bowel disease, Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis. In embodiments, the disease, disorder or condition is one that is mediated by CCR4. In embodiments, the CCR4-mediated disease, disorder or condition is one of asthma, COPD, rhinitis, idiopathic pulmonary fibrosis, psoriasis and contact dermatitis. In embodiments the disease or disorder is pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development. The methods generally involve administering to a patient in need of such treatment or prevention a therapeutically effective amount of the crystalline form A and/or the crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate described herein.

In another aspect, provided are methods of making crystalline forms of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

In embodiments, the methods for making the crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate described herein are provided. In embodiments, the methods for making the crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate described herein are provided.

5. BRIEF DESCRIPTION OF THE FIGURES

6. DETAILED DESCRIPTION

6.1 Definitions

Figure 1:
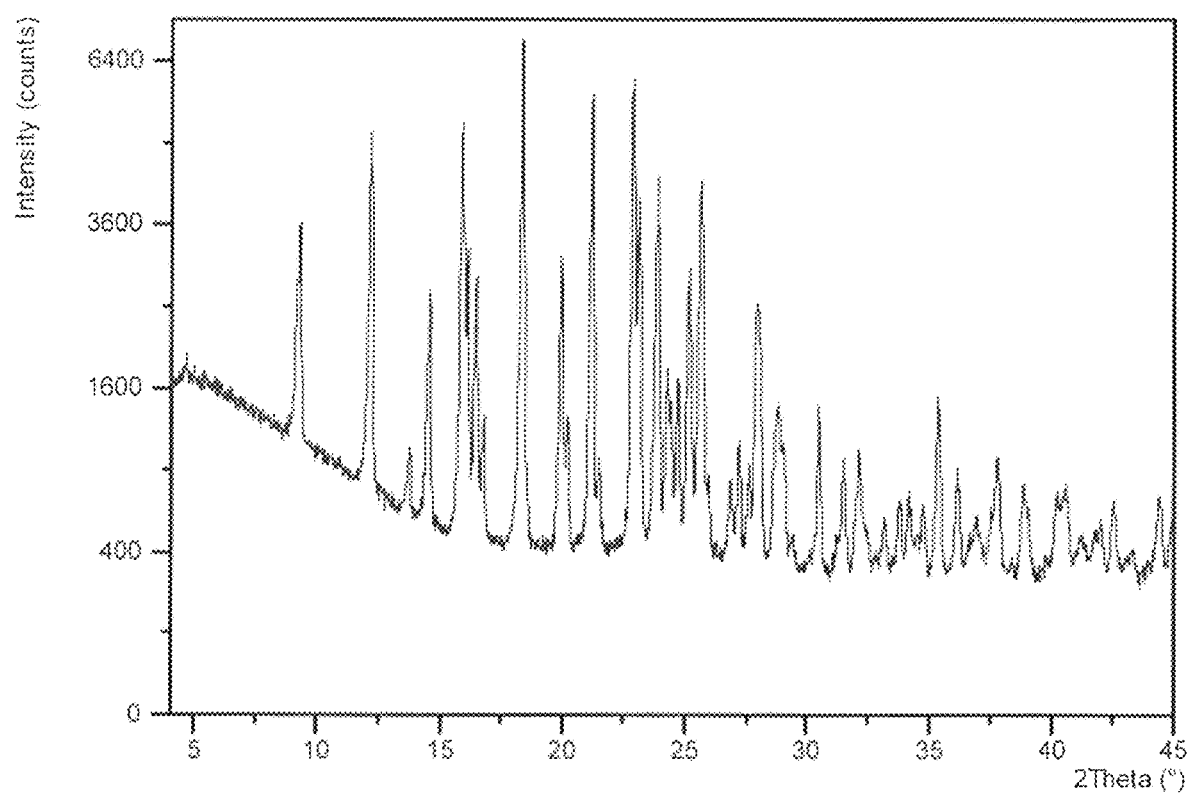
FIG. 1 illustrates an X-ray powder diffractogram of crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

As used herein, the term "pharmaceutically acceptable vehicle" refers to a diluent, adjuvant, excipient or carrier with which 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate can be administered to a patient in need thereof.

As used herein, the term "pharmaceutically acceptable salts" is meant to include salts of the compounds that are prepared with relatively nontoxic acids or bases, depending on the particular substituents found on the compounds. The crystalline compounds described herein are besylate salts. When compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds may contain both basic and acidic functionalities that allow the compounds to be converted into either base or acid addition salts.

As used herein, the terms "C-C chemokine receptor type 4" and "CCR4" refer to a protein (including homologs, isoforms, and functional fragments thereof) and is a high affinity receptor for the C-C-type chemokines (e.g., CCL2 (MCP-1), CCL4 (MIP-1), CCL5 (RANTES), CCL17 (TARC), and CCL22 (MDC)). It is referred to by a number of different names in the scientific literature, including "CC-CKR-4", "C-C CKR-4", "K5-5", "CD194", "CMKBR4", "ChemR13", "HGCN", and "14099". The term includes any recombinant or naturally-occurring form of CCR4 variants thereof that maintain CCR4 activity (e.g. within at least 30%, 40%, 50%, 60%, 70%, 80%, 90%, 95%, or 100% activity compared to wildtype CCR4). The term includes any mutant form of CCR4 variants (e.g., frameshift mutations) thereof that maintain CCR4 activity (e.g. within at least 30%, 40%, 50%, 60%, 70%, 80%, 90%, 95%, or 100% activity compared to wildtype CCR4). In embodiments, the CCR4 protein encoded by the CCR4 gene has the amino acid sequence set forth in or corresponding to Entrez 1233, UniProt P51679, or RefSeq (protein) NP 005499.1. In embodiments, the CCR4 gene has the nucleic acid sequence set forth in RefSeq (mRNA) NM 005508. In embodiments, the amino acid sequence or nucleic acid sequence is the sequence known at the time of filing of the present application. In embodiments, the sequence corresponds to GI:5031627. In embodiments, the sequence corresponds to NP_005499.1. In embodiments, the sequence corresponds to NM_005508.4. In embodiments, the sequence corresponds to GI:48762930. In embodiments, the CCR4 is a human CCR4, such as a human cancer causing CCR4. Though frequently found on dendritic cells, macrophages, NK cells, platelets, and basophils, CCR4 is predominantly associated with T cells. It plays a role in the progression of multiple inflammation-related disorders, and, as described herein, has also been implicated in a number of other conditions. The genomic sequence of CCR4 is present on chromosome 3 (NC_000003.12), and the CCR4 gene is conserved in a number of species, including chimpanzee, Rhesus monkey, dog, cow, mouse, rat, chicken, and zebrafish. The CCR4 polypeptide comprises 360 amino acid residues (NP_005499.1), and, like other chemokine receptors, CCR4 is a G protein-coupled receptor found on the surface of leukocytes (see Horuk (1994) Trends Pharm. Sci. 15:159-165).

As used herein, the term "CCR4 inhibitor" refers to a compound (e.g., compounds described herein) that reduces the activity of CCR4 when compared to a control, such as absence of the compound or a compound with known inactivity.

As used herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As used herein, the terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As used herein, the term "inhibition," "inhibit", "inhibiting," and the like, in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

As used herein, the terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

As used herein, the terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, nasopharangeal carcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound (e.g., CCR4 inhibitor) of the present invention may be particularly efficacious (due to, for example, limitations of current therapies) are described in more detail hereafter.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head and neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, nasopharangeal carcinoma, head and neck squamous cell carcinoma, breast invasive carcinoma, lung adenocarcinoma, lung squamous cell carcinoma, Hodgkin's Disease, Hodgkin lymphoma, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

As used herein, the term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

As used herein, the term "modulator" refers to a composition that increases or decreases the level of a target molecule or the function of a target molecule or the physical state of the target of the molecule. In embodiments, a CCR4 associated disease modulator is a compound that reduces the severity of one or more symptoms of a disease associated with CCR4 (e.g. cancer, inflammatory disease, autoimmune disease, or infectious disease). A CCR4 modulator is a compound that increases or decreases the activity or function or level of activity or level of function of CCR4. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate", "modulation" and the like refer to the ability of a molecule (e.g., an activator or an inhibitor) to increase or decrease the function or activity of CCR4, either directly or indirectly, relative to the absence of the molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In embodiments, a patient is human. The terms "human" and "patient" are used interchangeably herein.

As used herein, the term "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations.

An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CCR4 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

By "co-administer" it is meant that a composition described herein is administered at the same time, just prior to, or just after the administration of one or more additional therapies. The compounds of the invention can be administered alone or can be coadministered to the patient. For example, a compound of the invention may be co-administered with an anti-cancer agent in the treatment of a cancer. Coadministration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

As used herein, the term "anti-cancer agent" refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. In embodiments, an anti-cancer agent includes, but is not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixmab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pembrolizumab; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bi s-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), pembrolizumab humanized antibody, immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In one embodiment, a crystalline compound disclosed herein is coadminstered with pembrolizumab to a patient in the treatment of cancer.

As used herein, the term "chemotherapeutic" or "chemotherapeutic agent" is used in accordance with its plain ordinary meaning and refers to a chemical composition or compound having antineoplastic properties or the ability to inhibit the growth or proliferation of cells. In embodiments, the chemotherapeutic agent is an antiproliferative/antineoplastic drug, an antimetabolite, an antitumour antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5.alpha.-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody.

As used herein, the term "anti-inflammatory agent" is used in accordance with its plain ordinary meaning and refers to a composition (e.g. compound, drug, antagonist, inhibitor, modulator) used in any way to reduce inflammation or swelling. In embodiments, an anti-inflammatory agent is an agent identified herein having utility in methods of treating an inflammatory disease or disorder. In embodiments, an anti-inflammatory agent is an agent approved by the FDA or similar regulatory agency of a country other than the USA, for reducing swelling and inflammation. In embodiments, the anti-inflammatory agent is thalidomide or a derivative thereof, a retinoid, dithranol or calcipotriol, a non-steroidal anti-inflammatory agent (hereinafter NSAID) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

As used herein, the term "solid form" refers to a form of a compound in which the atoms or molecules are tightly connected via chemical bonds so that its shape and volume are relatively stable.

As used herein, the term "crystalline form of a compound" refers to a compound having a crystalline structure, i.e., the compound constituents are arranged in a highly ordered microscopic structure forming a crystal lattice that extends in all directions.

As used herein, the term "amorphous form of a compound" refers to a compound having an amorphous structure, i.e., structure that lacks the long-range order of crystalline compound.

As used herein, the term "therapeutic index" refers to a dose ratio between toxic and therapeutic effect.

6.2 Crystalline Compounds

When herein reference is made to a compound according to the invention being crystalline, suitably the degree of crystallinity as determined by X-ray powder diffraction data, is for example greater than about 60%, such as greater than about 80%, particularly greater than about 90%, more particularly greater than about 95%. In embodiments of the invention, the degree of crystallinity as determined by X-ray powder diffraction data is greater than about 98%, wherein the % crystallinity refers to the % by weight of the total sample mass which is crystalline.

Suitably, a crystalline modification of a compound according to the invention is substantially free from other crystalline modifications of the compound. Suitably, a described crystalline modification of a compound described herein includes less than, for example, 20%, 15%, 10%, 5%, 3% or particularly, less than 1% by weight of other crystalline forms of that compound.

The crystalline compound disclosed herein is a benzene sulfonate salt, also referred to as a besylate salt of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol. The besylate salt form of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol can be made by reacting the free base, 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol, with benzene sulfonic acid. The free base of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol can be made according to procedures disclosed in Example 42 of Beck et al., U.S. Pat. No. 10,179,787 issued Jan. 15, 2019 and in Beck et al., International Application WO 2018/022992 published Feb. 1, 2018, both entitled, "Chemokine Receptor Modulators and Uses Thereof."

6.2. A. Crystalline Form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and Preparation Thereof In embodiments, provided is a crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has characteristic absorption peaks at $18.4°\pm0.3°$, $22.9°\pm0.3°$, $21.2°\pm0.3°$, and $15.9°\pm0.3°$ in an X-ray powder diffractogram using Cu Kα radiation.

In another embodiment, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has characteristic absorption peaks at $18.4°\pm0.3°$, $22.9°\pm0.3°$, $21.2°\pm0.3°$, $15.9°\pm0.3°$, $12.2°\pm0.3°$, $23.8°\pm0.3°$, and $25.6°\pm0.3°$ in an X-ray powder diffractogram using Cu Kα radiation.

In another embodiment, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has characteristic absorption peaks at $18.4°\pm0.3°$, $22.9°\pm0.3°$, $21.2°\pm0.3°$, $15.9°\pm0.3°$, $12.2°\pm0.3°$, $23.8°\pm0.3°$, $25.6°\pm0.3°$, $23.1°\pm0.3°$, $20.0°\pm0.3°$, and $16.2°\pm0.3°$ in an X-ray powder diffractogram using Cu Kα radiation.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 159° C. and about 183° C. In other embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 165° C. and about 177° C. In still other embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 168° C. and about 174° C. In still other embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 169° C. and about 173° C. In still other embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 170° C. and about 173° C. In still other embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 171° C. and about 173° C. In still other embodiments, crystalline form A of 2-((R)-3-(1-(1-((R)-1-(2,4-Dichlorophenyl)ethyl)-3-(trifluoromethyl)-

1H-pyrazolo[3,4-b]pyrazin-6-yl)azetidin-3-yl)piperidin-1-yl)ethan-1-ol benzene sulfonate has a melting point of 172° C.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be prepared by first adding 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate to a solvent to form a solution or suspension. As used herein, the terms solution and suspension are used interchangeably and are meant to include circumstances where 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is placed in a solvent or solvent mixture regardless of solubility. The solvent used in crystallization may be either a homogenous solvent, a combination of solvents, or a solvent or solvent combination in which the 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate exhibits temperature dependent solubility.

In embodiments, the dissolution process is carried out at elevated temperature. In embodiments, the dissolution process is carried out at temperatures up to and including the boiling point of the solvent or solvent combination. In embodiments, 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is dissolved in a solvent or solvent mixture with heating and optionally, shaking and stirring. In embodiments, the heated solution may be kept at elevated temperature to ensure complete dissolution of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, the heated solution may also be filtered at elevated temperature to remove any undissolved components.

In embodiments, the solution is cooled slowly to provide crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is separated from residual solvent by filtration and/or drying under reduced pressure. Other methods, known to those of skill in crystallization arts, (e.g., solvent evaporation, drowning, chemical reaction, seeding with a small quantity of the desired crystal form, etc.) may also be employed to provide crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

In embodiments, 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is dissolved in a solvent at an elevated temperature, the solution is then cooled to room temperature to provide crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a high melting point.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has low hygroscopicity.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has good solubility.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has good bioavailability.

In embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has demonstrated outstanding stability after 36 months of storage at room temperature.

6.2. B. Crystalline Form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and Preparation Thereof In one embodiment, provided is crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene. In embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has characteristic absorption peaks at 12.5°±0.3°, 14.6°±0.3°, 22.3°±0.3°, and 13.3°±0.3° in an X-ray powder diffractogram using Cu Kα radiation.

In another embodiment, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has characteristic absorption peaks at 12.5°±0.3°, 14.6°±0.3°, 22.3°±0.3°, 13.3°±0.3°, 15.8°±0.3°, 24.5°±0.3°, and 4.5°±0.3° in an X-ray powder diffractogram using Cu Kα radiation.

In another embodiment, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has characteristic absorption peaks at 12.5°±0.3°, 14.6°±0.3°, 22.3°±0.3°, 13.3°±0.3°, 15.8°±0.3°, 24.5°±0.3°, 4.5°±0.3°, 22.8°±0.3°, 10.6°±0.3°, and 18.6°±0.3° in an X-ray powder diffractogram using Cu Kα radiation.

In embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 105° C. and about 129° C. In other embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 111° C. and about 123° C. In still other embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 114° C. and about 120° C. In still other embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 115° C. and about 119° C. In still other embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 116° C. and about 119° C. In still other embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate has a melting point between about 116° C. and about 118° C.

In embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be prepared by first adding 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate to a solvent to form a solution or suspension. As used herein, the terms solution and suspension are used interchangeably and are meant to include circumstances where 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is placed in a solvent or solvent mixture regardless of solubility. The solvent used in crystallization may be either a homogenous solvent, a combination of solvents, or a solvent or solvent combination in which the 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate exhibits temperature dependent solubility.

In embodiments, the dissolution process is carried out at elevated temperature. In embodiments, the dissolution process is carried out at temperatures up to and including the boiling point of the solvent or solvent combination. In embodiments, 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is dissolved in a solvent or solvent mixture with heating and optionally, shaking and stirring. In embodiments, the heated solution may be kept at elevated temperature to ensure complete dissolution of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, the heated solution may also be filtered at elevated temperature to remove any undissolved components.

In embodiments, the solution is cooled slowly to provide crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is separated from residual solvent by filtration and/or drying under reduced pressure. Other methods, known to those of skill in crystallization arts, (e.g., solvent evaporation, drowning, chemical reaction, seeding with a small quantity of the desired crystal form, etc.) may also be employed to provide crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

6.3 Therapeutic Uses

In embodiments, provided are methods of treatment and prophylaxis of a CCR4-mediated disease, disorder or condition comprising administering to a patient in need thereof a therapeutically effective amount of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof. In embodiments, the patient is an animal. In embodiments, the patient is a mammal. In embodiments, the patient is a human.

In embodiments, provided is a method of treating an immune-, inflammatory-, or cancer-related disease or disorder, comprising administering to a patient in need of such treatment a crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

In embodiments, provided is a method of treating an immune-, inflammatory-, or cancer-related disease or disorder, comprising administering to a patient in need of such treatment a pharmaceutical composition comprising a crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be administered to a patient, in particular a human patient, suffering from an allergy-related disorder (e.g., hypersensitivity and anaphylactic responses); a gastrointestinal disorder (e.g., inflammatory bowel disease, Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis.

In embodiments, the CCR4-mediated disease, disorder or condition is asthma, COPD, rhinitis, idiopathic pulmonary fibrosis, psoriasis and contact dermatitis. In embodiments the disease or disorder is pulmonary fibrosis, hepatic inflammation, asthma, atopic dermatitis, cancer (e.g., thyroid carcinoma, nasopharangeal carcinoma, Hodgkin lymphoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development.

Further, in certain embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are administered to a patient, preferably a human, as a preventative measure against various diseases or disorders. Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be administered as a preventative measure to a patient having a predisposition for an allergy-related disorder (e.g., hypersensitivity and anaphylactic responses); a gastrointestinal disorder (e.g., inflammatory bowel disease, Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis; asthma, COPD, rhinitis, idiopathic pulmonary fibrosis, psoriasis and contact dermatitis; pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development. Accordingly, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be used for the prevention of one disease or disorder and concurrently treating another (e.g., prevention of psoriasis while treating cancer; prevention of asthma while treating contact dermatitis).

The suitability of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof in treating the above-mentioned diseases and disorders may be determined by methods known in the art. Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be used to treat or prevent the above-mentioned diseases and disorders using known procedures described in the art.

6.4 Modes of Administration

In embodiments, provided are methods of treatment and prophylaxis of a CCR4-mediated disease, disorder or condition comprising administering to a patient in need thereof a therapeutically effective amount of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof. In embodiments, the patient is an animal. In embodiments, the patient is a mammal. In embodiments, the patient is a human.

Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are useful for the treatment or prevention of an allergy-related disorder (e.g., hypersensitivity and anaphylactic responses); a gastrointestinal disorder (e.g., inflammatory bowel disease, Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis.

In embodiments, the CCR4-mediated disease, disorder or condition is asthma, COPD, rhinitis, idiopathic pulmonary fibrosis, psoriasis and contact dermatitis. In embodiments the disease or disorder is pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development.

Further, in certain embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are administered to a patient, preferably a human, as a preventative measure against various diseases or disorders. Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be administered as a preventative measure to a patient having a predisposition for an allergy-related disorder (e.g., hypersensitivity and anaphylactic responses); a gastrointestinal disorder (e.g., inflammatory bowel disease, Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis; asthma, COPD, rhinitis, idiopathic pulmonary fibrosis, psoriasis and contact dermatitis; pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development. Accordingly, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be used for the prevention of one disease or disorder and concurrently treating another (e.g., prevention of psoriasis while treating cancer; prevention of asthma while treating contact dermatitis).

Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes or skin.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are administered orally. Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). In embodiments, the administration can be systemic or local. Various delivery systems are known, (e.g., encapsulation in liposomes, microparticles, microcapsules, capsules, etc.) that can be used to administer crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof can be delivered via sustained release systems. In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof can be delivered via oral sustained release systems. In one embodiment, the oral sustained release system is a pump (Langer, supra; Sefton, 1987, *CRC Crit Ref Biomed. Eng.* 14:201; Saudek et al., 1989, *N. Engl. J. Med.* 321:574).

In other embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof can be delivered using polymeric materials ("Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J. Macromol. Sci. Rev. Macromol. Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for oral sustained release delivery. Polymers suitable to be used for oral delivery of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof include, but are not limited to, sodium carboxymethylcellulose, hydroxypropylcellulose, hydroxypropylmethylcellulose and hydroxyethylcellulose. In one embodiment, the polymer is hydroxypropylmethylcellulose. Other cellulose ethers have been described (Alderman, *Int. J. Pharm. Tech. &Prod. Mfr.* 1984, 5(3) 1-9). Factors affecting drug release are well known to a skilled artisan and have been described in the art (Bamba et al., *Int. J. Pharm.* 1979, 2, 307).

In other embodiments, enteric-coated preparations can be used for oral sustained release administration of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof. Coating materials suitable to be used for oral delivery of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl) ethan-1-ol benzene sulfonate and/or pharmaceutical compositions thereof include, but are not limited to, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof (Verma et al., *Drug Dev. Ind. Pharm.* 2000, 26:695-708). In embodiments, OROS™ osmotic devices are used for oral sustained release delivery devices of crystalline 2-((R)-3-(1-(1-((R)-1-(2,4-Dichlorophenyl)ethyl)-3-(trifluoromethyl)-1H-pyrazolo[3,4-b] pyrazin-6-yl)azetidin-3-yl)piperidin-1-yl)ethan-1-ol benzene sulfonate and/or pharmaceutical compositions thereof (Theeuwes et al., U.S. Pat. No. 3,845,770; Theeuwes et al., U.S. Pat. No. 3,916,899).

In yet other embodiments, a controlled-release system can be placed in proximity of the target of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof, thus requiring only a fraction of the systemic dose (e.g., Goodson, in "Medical Applications of Controlled Release," supra, vol. 2, pp. 115-138 (1984)). Other controlled-release systems discussed in Langer, 1990, *Science* 249:1527-1533 may also be used.

When used to treat or prevent the CCR4-mediated disease, disorder or condition, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be administered or applied singly, or in combination with other agents. In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may also be administered or applied singly or in combination with other pharmaceutically active agents, including, in the case of treating cancer, another anticancer/chemotherapeutic agent(s).

In embodiments, an anti-cancer agent includes, but is not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, pembrolizumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixmab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Carib-aeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

6.5 Pharmaceutical Compositions

In embodiments, provided are pharmaceutical compositions comprising a therapeutically effective amount of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and a suitable amount of a pharmaceutically acceptable vehicle, so as to provide the form for proper administration to a patient. In embodiments, when administered to a patient, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and pharmaceutically acceptable vehicles are sterile. In embodiments, when crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is administered intravenously, the vehicle is water. In other embodiments, saline solutions and aqueous dextrose and glycerol solutions are used as liquid vehicles for injectable solutions. In yet other embodiments, suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. In other embodiments, the pharmaceutical compositions of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate contain wetting or emulsifying agents or pH buffering agents. In other embodiments, the pharmaceutical compositions of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate contain auxiliary, stabilizing, thickening, lubricating and coloring agents.

In embodiments, pharmaceutical compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be manufactured by means of conventional mixing, dissolving, granulating, dragee-making, levigating, emulsifying, encapsulating, entrapping or lyophilizing processes. In embodiments, pharmaceutical compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be formulated in conventional manner using one or more physiologically acceptable carriers, diluents, excipients or auxiliaries, which facilitate processing of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate into preparations which can be used pharmaceutically. As appreciate by those skilled in the art, proper formulation is dependent upon the route of administration chosen.

In embodiments, pharmaceutical compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is a solution, suspension, emulsion, tablet, pill, pellet, capsule, capsule containing liquids, powder, sustained-release formulation, suppository, emulsion, aerosol, spray, or any other form suitable for use. In embodiments, the pharmaceutically acceptable vehicle is a capsule (e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In embodiments, pharmaceutical compositions of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)

piperidin-1-yl)ethan-1-ol benzene sulfonate are formulated for oral delivery. In embodiments, pharmaceutical compositions of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate are formulated for oral sustained release administration.

In embodiments, pharmaceutical compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen or cherry coloring agents and preserving agents, to provide a pharmaceutically palatable preparation. Moreover, where in tablet or pill form, the pharmaceutical compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be coated to delay disintegration and absorption in the gastrointestinal tract, thereby providing a sustained action over an extended period of time. Selectively permeable membranes surrounding an osmotically active driving compound are also suitable for orally administering the compounds and compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate disclosed herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate can include standard vehicles such as mannitol, lactose, starch, magnesium stearate, sodium saccharine, cellulose, magnesium carbonate, etc. In embodiments, such vehicles are of pharmaceutical grade.

In embodiments, for oral liquid preparations such as suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. In embodiments, flavoring agents, preservatives, coloring agents, bile salts, acylcarnitines and the like are additionally added.

Pharmaceutical compositions for administration via other routes may also be contemplated. In embodiments, for buccal administration, the compositions comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may take the form of tablets, lozenges, etc. formulated in conventional manner. Liquid drug formulations suitable for use with nebulizers and liquid spray devices and EHD aerosol devices will typically include crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl) ethan-1-ol benzene sulfonate with a pharmaceutically acceptable vehicle. In embodiments, the pharmaceutically acceptable vehicle is a liquid such as alcohol, water, polyethylene glycol or perfluorocarbon. In embodiments, another material may be added to alter the aerosol properties of the solution or suspension of the compounds disclosed herein. In embodiments, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). In embodiments, Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may also be formulated in rectal or vaginal compositions such as suppositories or retention enemas, e.g., containing conventional suppository bases such as cocoa butter or other glycerides. In further embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may also be formulated as a depot preparation. Such long acting formulations may be administered by implantation (for example subcutaneously or intramuscularly) or by intramuscular injection. In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be formulated with suitable polymeric or hydrophobic materials (for example, as an emulsion in an acceptable oil) or ion exchange resins, or as sparingly soluble derivatives.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is formulated as a pure active agent. In other embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is formulated as a mixture with other crystalline forms of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, the pharmaceutical compositions provided herein comprise form A of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, the pharmaceutical compositions provided herein comprise form B of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, the pharmaceutical compositions provided herein comprise the mixture of form A and B of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

In embodiments, the pharmaceutical composition of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is formulated as an oral tablet dosage form.

In embodiments, the pharmaceutical composition of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin- 3-yl)piperidin-1-yl)ethan-1-ol benzene sulfonate in oral tablet dosage form comprises 75 mg of the crystalline compound.

In embodiments, the pharmaceutical composition of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate in oral tablet dosage form comprises 25 mg of the crystalline compound.

In embodiments, the pharmaceutical composition of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate comprises a wetting agent. In embodiments, the wetting agent is sodium lauryl sulfate (SLS).

In embodiments, the pharmaceutical composition of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate comprises a water soluble excipient. In embodiments, the water soluble excipient is lactose mono-hydrate. In embodiments, the water soluble excipient is at least 50% by weight of the oral tablet dosage form.

In embodiments, the pharmaceutical composition of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate comprises a disintegrant. In embodiments, the disintegrant is croscarmellose sodium.

6.6 Dosages

Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof, will be used in an amount effective to achieve the intended purpose. In embodiments, for use to treat or prevent CCR4-mediated diseases or disorders disclosed herein, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are administered or applied in a therapeutically effective amount.

The amount of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof administered will be dependent on, among other factors, the subject being treated, the weight of the subject, the severity of the affliction, the manner of administration and the judgment of the prescribing physician.

In embodiments, the dosage of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be delivered in a pharmaceutical composition by a single administration. In embodiments, the dosage of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be delivered in a pharmaceutical composition by multiple applications. In embodiments, the dosage of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be delivered in a pharmaceutical composition by controlled release. In embodiments, the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are delivered by oral sustained release administration. In particular embodiments, the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are administered twice per day. In embodiments, the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are administered once per day. In embodiments, dosing may be repeated intermittently. In embodiments, dosing may be provided alone. In embodiments, dosing may be provided in combination with other drugs. In embodiments, dosing may continue as long as required for effective treatment of the CCR4-mediated disease state or disorder described herein.

In embodiments, the dose of the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be adjusted to provide between about 25 mg/day and about 500 mg/day. In other embodiments, the dose of the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be adjusted to provide between about 50 mg/day and about 150 mg/day. In still other embodiments, the dose of the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be adjusted to provide between about 75 mg/day and about 125 mg/day. Dosage ranges may be readily determined by methods known to the skilled artisan.

The crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are assayed in vitro and in vivo, for the desired therapeutic or prophylactic activity, prior to use in humans. In embodiments, a therapeutically effective dose of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof described herein will provide therapeutic benefit without causing substantial toxicity. Toxicity of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof may be determined using standard pharmaceutical procedures and may be readily ascertained by the skilled artisan. In embodiments, the dosage of crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof described herein is within a range of circulating concentrations that include an effective dose with little or no toxicity.

6.7 Combination Therapy

In certain embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are used in combination with at least one other therapeutic agent. In embodiments, co-administration includes administering one therapeutic agent within 0.5, 1, 2, 4, 6, 8, 10, 12, 16, 20, 24 hours, 2 days, 4 days, 1 week or 1 month of a second therapeutic agent. In embodiments, co-administration includes administering two therapeutic agents simultaneously, or approximately simultaneously (e.g., within about 1, 5, 10, 15, 20, or 30 minutes of each other). In embodiments, co-administration includes administering two therapeutic agents sequentially in any order. In embodiments, co-administration can be accomplished by co-formulation, i.e., preparing a single pharmaceutical composition including both therapeutic agents. In other embodiments, the therapeutic agents can be formulated separately. In another embodiment, the active and/or adjunctive agents may be linked or conjugated to one another. In embodiments, the compounds described herein may be combined with treatments for CCR4-mediated diseases disclosed herein.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof and the other therapeutic agent acts additively. In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof and the other therapeutic agent acts synergistically.

In embodiments, the other therapeutic agent is an anticancer agent, a chemotherapeutic agent, or an anti-inflammatory agent.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are used in combination with an anticancer agent. In embodiments, the anticancer agent is MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine octfosate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitrabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, pembrolizumab (Keytruda™), EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are used in combination with a chemotherapeutic agent. In embodiments, the chemotherapeutic agent is an antiproliferative/antineoplastic drug, an antimetabolite, an antitumour antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5.alpha.-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody.

In embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and/or pharmaceutical compositions thereof are used in combination with an anti-inflammatory agent. In embodiments, the anti-inflammatory agent is thalidomide or a derivative thereof, a retinoid, dithranol or calcipotriol, a non-steroidal anti-inflammatory agent (hereinafter NSAID) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

In embodiments, a pharmaceutical composition comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is administered concurrently with the administration of another therapeutic agent, which can be part of the same pharmaceutical composition as the crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In embodiments, a pharmaceutical composition comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is administered concurrently with the administration of another therapeutic agent, which can be part of a different pharmaceutical composition. In other embodiments, a pharmaceutical composition comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is administered prior to administration of another therapeutic agent. In other embodiments, a pharmaceutical composition comprising crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate is administered subsequent with administration of another therapeutic agent.

In other embodiments, the another therapeutic agent is pembrolizumab.

In other embodiments, crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be administered in combination with an amorphous form of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate. In other embodiments, crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate may be administered in combination with crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

7. NUMBERED EMBODIMENTS

Embodiment 1. Compound 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate in crystalline form.

Embodiment 2. The compound of embodiment 1, having characteristic absorption peaks (2θ) at 18.4°±0.3°, 22.9°±0.3°, 21.2°±0.3°, and 15.9°±0.3° in an X-ray powder diffractogram using Cu Kα radiation.

Embodiment 3. The compound of embodiment 1, having characteristic absorption peaks (2θ) at 12.2°±0.3°, 23.8°±0.3°, and 25.6°±0.3° in an X-ray powder diffractogram using Cu Kα radiation.

Embodiment 4. The compound of embodiment 1, having characteristic absorption peaks (2θ) at 23.1°±0.3°, 20.0°±0.3°, and 16.2°±0.3° in an X-ray powder diffractogram using Cu Kα radiation.

Embodiment 5. The compound of embodiment 1, having an X-ray powder diffractogram using Cu Kα radiation illustrated in FIG. 1.

Embodiment 6. The compound of embodiment 1, having a melting point between about 170° C. and about 173° C. as determined by differential scanning calorimetry at a scan rate of 5° C./minute.

Embodiment 7. The compound of embodiment 2, having a characteristic absorption peak (2θ) at 12.2°±0.3° in an X-ray powder diffractogram using Cu Kα radiation.

Embodiment 8. The compound of embodiment 2, having a characteristic absorption peak (2θ) at 23.8°±0.3° in an X-ray powder diffractogram using Cu Kα radiation.

Embodiment 9. The compound of embodiment 2, having a characteristic absorption peak (2θ) at 25.6°±0.3° in an X-ray powder diffractogram using Cu Kα radiation.

Embodiment 10. The compound of embodiment 2, having a characteristic absorption peak (2θ) at 23.1°±0.3° in an X-ray powder diffractogram using Cu Kα radiation.

Embodiment 11. The compound of embodiment 2, having a characteristic absorption peak (2θ) at 20.0°±0.3° in an X-ray powder diffractogram using Cu Kα radiation.

Embodiment 12. The compound of embodiment 2, having a characteristic absorption peak (2θ) at 16.2°±0.3° in an X-ray powder diffractogram using Cu Kα radiation.

Embodiment 13. The compound of embodiment 1, having characteristic absorption peaks (2θ) at 12.5°±0.3°, 14.6°±0.3°, 22.3°±0.3°, and 13.3°±0.3° in an X-ray powder diffractogram using Cu Kα radiation.

Embodiment 14. The compound of embodiment 13, having characteristic absorption peaks (2θ) at 15.8°±0.3°, 24.5°±0.3°, and 4.5°±0.3° in an X-ray powder diffractogram using Cu Kα radiation.

Embodiment 15. The compound of embodiment 14, having characteristic absorption peaks (2θ) at 22.8°±0.3°, 10.6°±0.3°, and 18.6°±0.3° in an X-ray powder diffractogram using Cu Kα radiation.

Embodiment 16. The compound of embodiment 1, having an X-ray powder diffractogram using Cu Kα radiation illustrated in FIG. 3.

Embodiment 17. The compound of embodiment 1, having a melting point between about 116° C. and about 119° C. as determined by differential scanning calorimetry at a scan rate of 5° C./minute.

Embodiment 18. The compound of embodiment 13, having a characteristic absorption peak (2θ) at 15.8°±0.3° in an X-ray powder diffractogram using Cu Kα radiation.

Embodiment 19. The compound of embodiment 13, having a characteristic absorption peak (2θ) at 24.5°±0.3° in an X-ray powder diffractogram using Cu Kα radiation.

Embodiment 20. The compound of embodiment 13, having a characteristic absorption peak (2θ) at 4.5°±0.3° in an X-ray powder diffractogram using Cu Kα radiation.

Embodiment 21. The compound of embodiment 13, having a characteristic absorption peak (2θ) at 22.8°±0.3° in an X-ray powder diffractogram using Cu Kα radiation.

Embodiment 22. The compound of embodiment 13, having a characteristic absorption peak (2θ) at 10.6°±0.3° in an X-ray powder diffractogram using Cu Kα radiation.

Embodiment 23. The compound of embodiment 13, having a characteristic absorption peak (2θ) at 18.6°±0.3° in an X-ray powder diffractogram using Cu Kα radiation.

Embodiment 24. A pharmaceutical composition comprising the crystalline compound of any one of embodiments 1 through 23 and a pharmaceutically acceptable vehicle.

Embodiment 25. A pharmaceutical composition comprising the crystalline compound of any one of embodiments 2 through 12 and a pharmaceutically acceptable vehicle.

Embodiment 26. A pharmaceutical composition comprising the crystalline compound of any one of embodiments 13 through 23 and a pharmaceutically acceptable vehicle.

Embodiment 27. The pharmaceutical composition of any one of embodiments 24 through 26, wherein the composition is an oral tablet dosage form.

Embodiment 28. The pharmaceutical composition of embodiment 27, wherein the composition comprising 75 mg of the crystalline compound.

Embodiment 29. The pharmaceutical composition of embodiment 27, wherein the composition comprising 25 mg of the crystalline compound.

Embodiment 30. The pharmaceutical composition of any one of embodiments 24 through 26, wherein the composition comprising a wetting agent.

Embodiment 31. The pharmaceutical composition of embodiment 30, wherein the wetting agent is sodium lauryl sulfate.

Embodiment 32. The pharmaceutical composition of any one of embodiments 24 through 26, wherein the composition comprising a water soluble excipient.

Embodiment 33. The pharmaceutical composition of embodiment 32, wherein the water soluble excipient is lactose mono-hydrate.

Embodiment 34. The pharmaceutical composition of embodiment 32, wherein the water soluble excipient is at least 50% by weight of said oral tablet dosage form.

Embodiment 35. The pharmaceutical composition of any one of embodiments 24 through 26, wherein the composition comprising disintegrant.

Embodiment 36. The pharmaceutical composition of embodiment 35, wherein the disintegrant is cros-carmellose sodium.

Embodiment 37. A method of treating an immune-, inflammatory-, or cancer-related disease or disorder, comprising administering to a patient in need of such treatment the crystalline compound of any one of embodiments 1 through 23.

Embodiment 38. A method of treating an immune-, inflammatory-, or cancer-related disease or disorder, comprising administering to a patient in need of such treatment the pharmaceutical composition of any one of embodiments 24 through 27.

Embodiment 39. The method of embodiment 37 or 38, wherein the disease or disorder is selected from allergy-related disorders, hypersensitivity, anaphylactic responses, gastrointestinal disorders, respiratory allergic diseases, hypersensitivity lung diseases, autoimmune diseases, inflammatory dermatoses, graft rejection, allograft rejection, transplant rejection, cancer, metastatic cancer, and neurodegenerative disease.

Embodiment 40. The method of embodiment 37 or 38, wherein the disease or disorder is selected from inflammatory bowel disease, Crohn's disease, ulcerative colitis, ileitis, enteritis, psoriasis, dermatitis, eczema, atopic dermatitis, allergic contact dermatitis, dermatomyositis, urticaria, pruritus, vasculitis, scleroderma, asthma, COPD, allergic rhinitis, arthritis (rheumatoid and psoriatic), multiple sclerosis, systemic lupus erythematosus, type I diabetes, glomerulonephritis, leukemia, lymphoma, gastric cancer, atherosclerosis, Alzheimer's disease, encephalitis, meningitis, hepatitis, nephritis, sepsis, sarcoidosis, allergic conjunctivitis, otitis, and sinusitis, idiopathic pulmonary fibrosis, contact dermatitis, pulmonary fibrosis, hepatic inflammation, asthma, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, nasopharangeal carcinoma, Hodgkin lymphoma, breast invasive carcinoma, lung adenocarcinoma, lung squamous cell carcinoma and granuloma development.

Embodiment 41. The method of embodiment 37 or 38, wherein the crystalline compound is co-administered with another therapeutic agent.

Embodiment 42. The method of embodiment 41, wherein the another therapeutic agent is pembrolizumab.

8. EXAMPLES

A stable, crystalline solid form of an organic molecule facilitates processing of the drug substance into a final drug product, e.g., an oral tablet dosage form, thus such a physical form is desired. Compound 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol first isolated in its freebase form, as outlined in U.S. Pat. No. 10,179,787. A crystalline solid form could not be produced from this freebase form. Initial attempts to form an HCl salt of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol also did not produce a crystalline solid.

A number of different salts of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol were made using other acids. Experiments to form salts were performed and evaluated using 14 different acids and 13 different solvents, either alone or in some combination, listed in Table 1 below.

TABLE 1

Survey of Acids and Solvents for 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol Salt Screen

| Acids | Solvents |
|---|---|
| P-Toluene sulfonic acid | Acetone |
| Methane sulfonic acid | Acetonitrile |
| Benzene sulfonic acid | 2-butanol |
| Phosphoric acid | 1,4-dioxane |
| Ethane Sulfonic acid | Ethanol |
| L-Tartaric acid | Ethyl acetate |
| Fumaric acid | Methanol |
| L-Malic acid | Methyl ethyl ketone |
| Hippuric acid | Isopropanol |
| Succinic acid | Methyl t-butyl ether |
| Sulfuric acid | THF |
| Mandelic acd | Toluene |

TABLE 1-continued

Survey of Acids and Solvents for 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol Salt Screen

| Acids | Solvents |
|---|---|
| Citric acid | |

This work revealed that only two acids produced a consistent solid form. The para-toluenesulfonic acid salt gave a stable crystalline salt with a single polymorph and a melting point of 220° C. This highly crystalline form was less soluble than the amorphous HCl salt. The lower solubility of the para-toluenesulfonic acid salt could inhibit the dissolution of the drug and prevent sufficient intestinal absorption. At pH 2, the kinetic solubility of the para-toluenesulfonic acid salt was only ⅕ of the same parameter of the HCl salt. The bioavailability of this salt in rats was less than half of that observed with the amorphous HCl salt. Low solubility and low bioavailability are not desireable properties for a pharmaceutical product.

The benzene sulfonic acid salt of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol was isolated, and two crystalline polymorphs were observed depending on crystallization conditions. The higher melting polymorph (170° C.) was obtained by using a mixture of methyl-t-butyl ether and ethanol and could be consistently isolated on production scale. The high melting point of this polymorph is advantageous as it makes it easier to manufacture at higher temperatures. This polymorph showed low hygroscopicity and greater solubility (411 µM) than the para-tolunenesulfonic acid salt (190 uM) in pH 2 water. The bioavailability of the benzenesulfonic acid salt in rats was greater than that observed for the para-toluenesulfonic acid salt of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol (34% vs 22%). Additionally, the benzenesulfonic acid salt of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol has demonstrated superior stability after 36 months of storage at room temperature. This unexpected combination of a reproducible formation, low hygroscopicity, high solubility, bioavailability and high stability on prolonged storage distinguishes this polymorph of the 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzenesulfonic acid salt making it ideal for pharmaceutical development.

The following examples describe in detail the preparation of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate and a crystalline form thereof. It will be apparent to those skilled in the art that many modifications, both to materials and methods, may be practiced without departing from the scope of the invention.

In the examples below, the following abbreviations have the following meanings. If an abbreviation is not defined, the generally accepted meaning applies.

Atm=atmosphere
Boc=tert-butyloxycarbonyl
Cbz=carbobenzyloxy
DCC=dicyclohexylcarbodiimide
DMAP=4-N,N-dimethylaminopyridine
DMF=N,N-dimethylformamide
DMSO=dimethylsulfoxide
Fmoc=9-fluorenylmethyloxycarbonyl
g=gram
h=hour
HPLC=high pressure liquid chromatography
L=liter
LC/MS=liquid chromatography/mass spectroscopy
M=molar
min=minute
mL=milliliter
mmol=millimoles
NHS=N-hydroxysuccinimide
THF=tetrahydrofuran
TFA=trifluoroacetic acid
TLC=thin layer chromatography
TMS=trimethylsilyl
µL=microliter
µM=micromolar
v/v=volume to volume Example 1. Synthesis of Non-Crystalline 2-((R)-3-(1-(1-((R)-1-(2,4-dichlorophenyl)ethyl)-3-(trifluoromethyl)-1H-pyrazolo[3,4-b]pyrazin-6-yl)azetidin-3-yl)piperidin-1-yl)ethan-1-ol benzenesulfonate

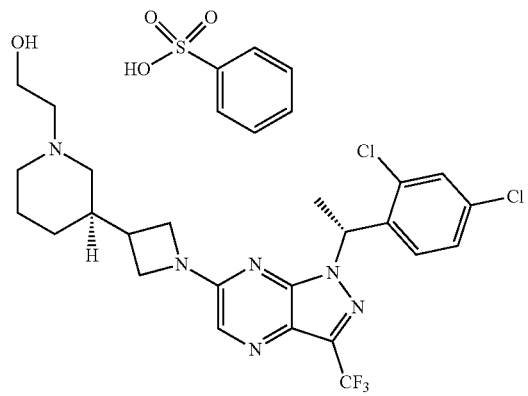 [SMILES: C[C@H](c1ccc(Cl)cc1Cl)n1nc(C(F)(F)F)c2ncc(N3CC([C@H]4CCCN(CCO)C4)C3)nc21 ; O=S(=O)(O)c1ccccc1]

2-[(3R)-3-[1-[1-[(1R)-1-(2,4-dichlorophenyl)ethyl]-3-(trifluoromethyl)pyrazolo[3,4-b]pyrazin-6-yl]azetidin-3-yl]-1-piperidyl]ethanol (1.0 g, 1.84 mmol) was dissolved in ethanol (10 mL) and then the solution was cooled to −10° C. (acetone/ice bath). Benzenesulfonic acid (291.09 mg, 1.84 mmol) was then added dropwise dissolved in Ethanol (10 mL) over 5 minutes. After the addition was completed, the reaction mixture was allowed to rise to 22° C. and stirred for 5 minutes. No precipitate was formed. The mixture was concentrated under reduced pressure and afforded the title compound as an off-white, non-crystalline solid (1.29 g, 99.9% yield). $^1$H NMR (400 MHz, Methanol-$d_4$): 7.90 (s, 1H), 7.85-7.78 (m, 2H), 7.47 (d, J=2.1 Hz, 1H), 7.41-7.33 (m, 4H), 7.29 (dd, J=8.5, 2.1 Hz, 1H), 6.44 (q, J=7.1 Hz, 1H), 4.35-4.19 (m, 2H), 4.05-3.94 (m, 2H), 3.90 (t, J=5.2 Hz, 2H), 3.62 (dd, J=26.7, 12.2 Hz, 2H), 3.29-3.20 (m, 2H), 2.94 (t, J=12.6 Hz, 1H), 2.77-2.58 (m, 2H), 2.22-2.08 (m, 1H), 2.07-1.94 (m, 2H), 1.91 (d, J=7.0 Hz, 3H), 1.83 (t, J=13.7 Hz, 1H), 1.28-1.12 (m, 1H). LCMS [M+H] 543.0.

Example 2. Synthesis of Crystalline Form A of 2-((R)-3-(1-(1-((R)-1-(2,4-dichlorophenyl)ethyl)-3-(trifluoromethyl)-1H-pyrazolo[3,4-b]pyrazin-6-yl) azetidin-3-yl)piperidin-1-yl)ethan-1-ol benzenesulfonate Non-crystalline 2-((R)-3-(1-(1-((R)-1-(2,4-dichlorophenyl)ethyl)-3-(trifluoromethyl)-1H-pyrazolo[3,4-b]pyrazin-6-yl)azetidin-3-yl)piperidin-1-yl)ethan-1-ol benzenesulfonate (230 g, 327.83 mmol) was charged in a 2 L flask. Ethanol (345 mL) was added and the flask was adapted with a reflux condenser and then heated to 60° C. where a clear solution was obtained. tert-Butyl methyl ether (1035 mL) was added at once and then the mixture was allowed to cool from 60° C. to room temperature (22° C.) over 2 hours to precipitate the product. The mixture was cooled to 0° C. and stirred for 1 hour at 0° C. and then the solids were isolated by filtration, rinsed with cold MTBE/EtOH (575 ml/115 mL), and dried under high vacuum at 55° C. until constant weight, and yielded 2-((R)-3-(1-(1-((R)-1-(2,4-dichlorophenyl)ethyl)-3-(trifluoromethyl)-1H-pyrazolo[3,4-b]pyrazin-6-yl)azetidin-3-yl)piperidin-1-yl)ethan-1-ol benzenesulfonate (216.35 g, 308.37 mmol, 94% yield) as a white crystalline solid (crystalline form A).

Example 3. Synthesis of Crystalline Form B of 2-((R)-3-(1-(1-((R)-1-(2,4-dichlorophenyl)ethyl)-3-(trifluoromethyl)-1H-pyrazolo[3,4-b]pyrazin-6-yl) azetidin-3-yl)piperidin-1-yl)ethan-1-ol benzenesulfonate Non-crystalline solid 2-((R)-3-(1-(1-((R)-1-(2,4-dichlorophenyl)ethyl)-3-(trifluoromethyl)-1H-pyrazolo[3,4-b] pyrazin-6-yl)azetidin-3-yl)piperidin-1-yl)ethan-1-ol benzene sulfonate (5 g) was added to 15 ml isopropyl alcohol (solvent) in a 100 ml flask. The mixture was first heated to 75° C., and then further heated to 81° C., to give a clear solution. Then 45 ml of methyl ethyl ketone (counter-solvent) was added to the solution. The solution was allowed to cool to 50° C. and then stirred for 30 minutes. The solution remained clear with no sign of solid crystal formation. A sample of the solution was withdrawn and agitated in a small vial, producing a precipitate. The slurry sample was returned to the original flask to seed but the slurry solids dissolved.

The solution was then allowed to cool to 35° C., then seeded in similar fashion as described above at 50° C., resulting in a slurry with solid crystals forming. The slurry was stirred at 35° C. for one hour, then allowed to cool to ambient temperature. The solids were isolated by filtration, rinsed with methyl ethyl ketone (2×5 ml), and then dried under vacuum at 50° C. until their weight remained constant, yielding 4.4 g of a white crystalline solid (crystalline form B).

Example 4. X-Ray Powder Diffraction Analysis of Crystalline Form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl) ethan-1-ol benzene sulfonate An X-ray powder diffractogram (XRPD) of a sample of crystalline form A of 2-((R)-3-(1-(1-((R)-1-(2,4-Dichlorophenyl)ethyl)-3-(trifluoromethyl)-1H-pyrazolo[3,4-b] pyrazin-6-yl)azetidin-3-yl)piperidin-1-yl)ethan-1-ol benzene sulfonate produced according to Example 2 above was measured with a Malvern Panalytical X'Pert Pro X-ray powder diffractometer using Cu Kα radiation with Bragg-Bentano geometry. The instrument was equipped with line-focused parallel beam optics utilizing a fixed divergent slit (0.5°) with anti-scatter slit (1°) and an X'Celerator detector. The tube voltage and amperage were set to 45 kV and 40 mA, respectively. The angular resolution of the goniometer was approximately 0.001°. The detector covered a range of 41° in 2-theta (2θ) with a step size of 0.0167°. Typical averaging time was 3.5 minutes for each XRPD pattern collected. A corundum sample (NIST 1976a) was used to calibrate the XRPD instrument. The sample produced the diffractogram pattern illustrated in FIG. 1. The diffractogram peaks from FIG. 1 are as shown in Table 2 below.

TABLE 2

| No. | Pos. [°2θ] | Height [cts] | Area [cts*°2θ] | Rel. Int. [%] | Tip Width | d-spacing [Å] | Derivation |
| --- | --- | --- | --- | --- | --- | --- | --- |
| 1 | 4.6437 | 225.46 | 22.32 | 3.58 | 0.1204 | 19.02950 | KA1 + KA2 |
| 2 | 9.1734 | 1589.67 | 157.39 | 25.27 | 0.1204 | 9.64058 | KA1 + KA2 |
| 3 | 9.3117 | 2448.19 | 201.99 | 38.91 | 0.1004 | 9.49779 | KA1 + KA2 |
| 4 | 12.2031 | 4100.52 | 676.64 | 65.18 | 0.2007 | 7.25308 | KA1 + KA2 |
| 5 | 13.7376 | 399.43 | 39.55 | 6.35 | 0.1204 | 6.44617 | KA1 + KA2 |
| 6 | 14.5706 | 2059.84 | 203.94 | 32.74 | 0.1204 | 6.07947 | KA1 + KA2 |
| 7 | 15.9071 | 4746.90 | 626.64 | 75.45 | 0.1606 | 5.57154 | KA1 + KA2 |
| 8 | 16.1516 | 2603.83 | 171.87 | 41.39 | 0.0803 | 5.48776 | KA1 + KA2 |
| 9 | 16.4698 | 2335.39 | 346.83 | 37.12 | 0.1807 | 5.38246 | KA1 + KA2 |
| 10 | 16.7865 | 882.32 | 87.36 | 14.02 | 0.1204 | 5.28160 | KA1 + KA2 |
| 11 | 18.3513 | 6291.40 | 830.53 | 100.00 | 0.1606 | 4.83461 | KA1 + KA2 |
| 12 | 19.9590 | 2701.87 | 312.09 | 42.95 | 0.1405 | 4.44867 | KA1 + KA2 |
| 13 | 20.2095 | 869.92 | 86.13 | 13.83 | 0.1204 | 4.39410 | KA1 + KA2 |
| 14 | 21.2084 | 5248.89 | 779.52 | 83.43 | 0.1807 | 4.18934 | KA1 + KA2 |
| 15 | 21.4877 | 558.49 | 46.08 | 8.88 | 0.1004 | 4.13552 | KA1 + KA2 |
| 16 | 22.8713 | 5663.96 | 654.24 | 90.03 | 0.1405 | 3.88837 | KA1 + KA2 |
| 17 | 23.1108 | 3460.47 | 456.82 | 55.00 | 0.1606 | 3.84862 | KA1 + KA2 |
| 18 | 23.8362 | 3833.93 | 506.12 | 60.94 | 0.1606 | 3.73311 | KA1 + KA2 |
| 19 | 24.2605 | 1371.19 | 135.76 | 21.79 | 0.1204 | 3.66878 | KA1 + KA2 |
| 20 | 24.4111 | 1020.72 | 84.22 | 16.22 | 0.1004 | 3.64649 | KA1 + KA2 |
| 21 | 24.7005 | 1291.97 | 170.55 | 20.54 | 0.1606 | 3.60441 | KA1 + KA2 |
| 22 | 25.1495 | 2585.12 | 383.92 | 41.09 | 0.1807 | 3.54107 | KA1 + KA2 |
| 23 | 25.5853 | 3563.71 | 705.67 | 56.64 | 0.2409 | 3.48174 | KA1 + KA2 |
| 24 | 25.9533 | 437.22 | 21.64 | 6.95 | 0.0602 | 3.43320 | KA1 + KA2 |

TABLE 2-continued

| No. | Pos. [°2θ] | Height [cts] | Area [cts*°2θ] | Rel. Int. [%] | Tip Width | d-spacing [Å] | Derivation |
|---|---|---|---|---|---|---|---|
| 25 | 26.8341 | 424.00 | 34.98 | 6.74 | 0.1004 | 3.32247 | KA1 + KA2 |
| 26 | 27.2051 | 728.40 | 84.14 | 11.58 | 0.1405 | 3.27799 | KA1 + KA2 |
| 27 | 27.6032 | 570.26 | 37.64 | 9.06 | 0.0803 | 3.23162 | KA1 + KA2 |
| 28 | 27.8996 | 2025.10 | 300.75 | 32.19 | 0.1807 | 3.19796 | KA1 + KA2 |
| 29 | 28.0540 | 1778.76 | 176.11 | 28.27 | 0.1204 | 3.18071 | KA1 + KA2 |
| 30 | 28.8767 | 958.13 | 110.67 | 15.23 | 0.1405 | 3.09193 | KA1 + KA2 |
| 31 | 29.0805 | 648.06 | 64.16 | 10.30 | 0.1204 | 3.07072 | KA1 + KA2 |
| 32 | 29.4474 | 96.04 | 15.85 | 1.53 | 0.2007 | 3.03329 | KA1 + KA2 |
| 33 | 30.4724 | 1081.84 | 89.26 | 17.20 | 0.1004 | 2.93356 | KA1 + KA2 |
| 34 | 31.2312 | 114.70 | 11.36 | 1.82 | 0.1204 | 2.86400 | KA1 + KA2 |
| 35 | 31.5248 | 639.88 | 52.79 | 10.17 | 0.1004 | 2.83799 | KA1 + KA2 |
| 36 | 32.1240 | 671.96 | 55.44 | 10.68 | 0.1004 | 2.78641 | KA1 + KA2 |
| 37 | 33.2310 | 203.45 | 23.50 | 3.23 | 0.1405 | 2.69607 | KA1 + KA2 |
| 38 | 33.8248 | 345.21 | 45.57 | 5.49 | 0.1606 | 2.65009 | KA1 + KA2 |
| 39 | 34.2014 | 416.24 | 48.08 | 6.62 | 0.1405 | 2.62177 | KA1 + KA2 |
| 40 | 34.7796 | 310.40 | 30.73 | 4.93 | 0.1204 | 2.57950 | KA1 + KA2 |
| 41 | 35.3613 | 1113.46 | 128.61 | 17.70 | 0.1405 | 2.53839 | KA1 + KA2 |
| 42 | 36.1596 | 568.07 | 28.12 | 9.03 | 0.0602 | 2.48416 | KA1 + KA2 |
| 43 | 36.9198 | 255.31 | 42.13 | 4.06 | 0.2007 | 2.43474 | KA1 + KA2 |
| 44 | 37.7754 | 684.32 | 79.05 | 10.88 | 0.1405 | 2.38153 | KA1 + KA2 |
| 45 | 38.3706 | 46.05 | 4.56 | 0.73 | 0.1204 | 2.34595 | KA1 + KA2 |
| 46 | 38.8391 | 470.77 | 46.61 | 7.48 | 0.1204 | 2.31873 | KA1 + KA2 |
| 47 | 40.2063 | 401.21 | 52.96 | 6.38 | 0.1606 | 2.24298 | KA1 + KA2 |
| 48 | 40.6062 | 436.21 | 86.38 | 6.93 | 0.2409 | 2.22181 | KA1 + KA2 |
| 49 | 41.1695 | 164.42 | 21.70 | 2.61 | 0.1606 | 2.19270 | KA1 + KA2 |
| 50 | 41.7064 | 172.37 | 17.07 | 2.74 | 0.1204 | 2.16571 | KA1 + KA2 |
| 51 | 41.9948 | 249.22 | 24.67 | 3.96 | 0.1204 | 2.15150 | KA1 + KA2 |
| 52 | 42.5124 | 377.43 | 31.14 | 6.00 | 0.1004 | 2.12649 | KA1 + KA2 |
| 53 | 43.3059 | 84.89 | 11.21 | 1.35 | 0.1606 | 2.08935 | KA1 + KA2 |
| 54 | 44.3504 | 417.56 | 34.45 | 6.64 | 0.1004 | 2.04254 | KA1 + KA2 |

Example 5. Differential Scanning Calorimetry (Melting Point) Analysis of Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate (Crystalline Form A)

Figure 2:
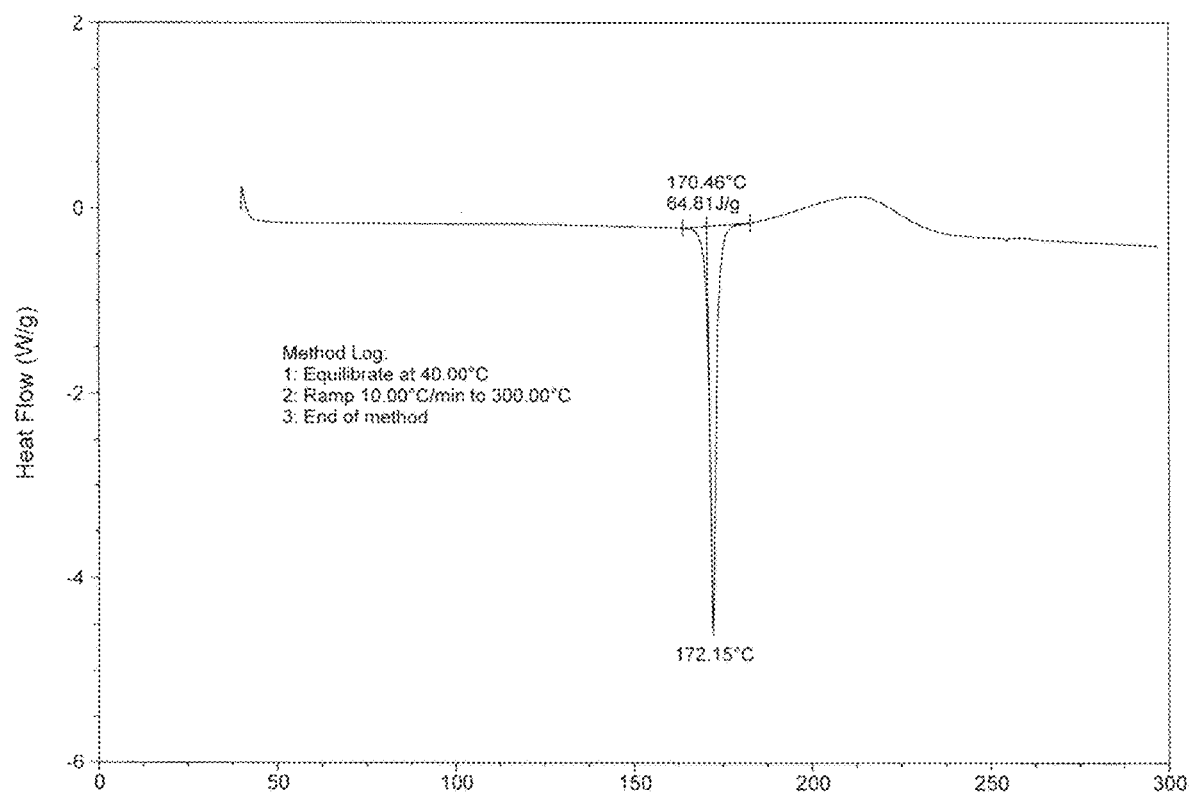
FIG. 2 illustrates a differential scanning calorimetry thermogram of crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

Differential scanning calorimetry (DSC) analysis of a crystalline sample of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate produced according to Example 2 above was measured using a TA Instruments Q2000 instrument, scanning from 40° C. to 250° C. at a scan rate of 10° C./minute. The material was run at the appropriate temperature program (Equilibration at Initial Temp, Isothermal, Ramp Rate, Final Temp) to produce the thermogram shown in FIG. 2. DSC analysis shows an endothermic transition with an onset temperature of 170° C. and a ΔH of 64.81 J/g.

Figure 3:
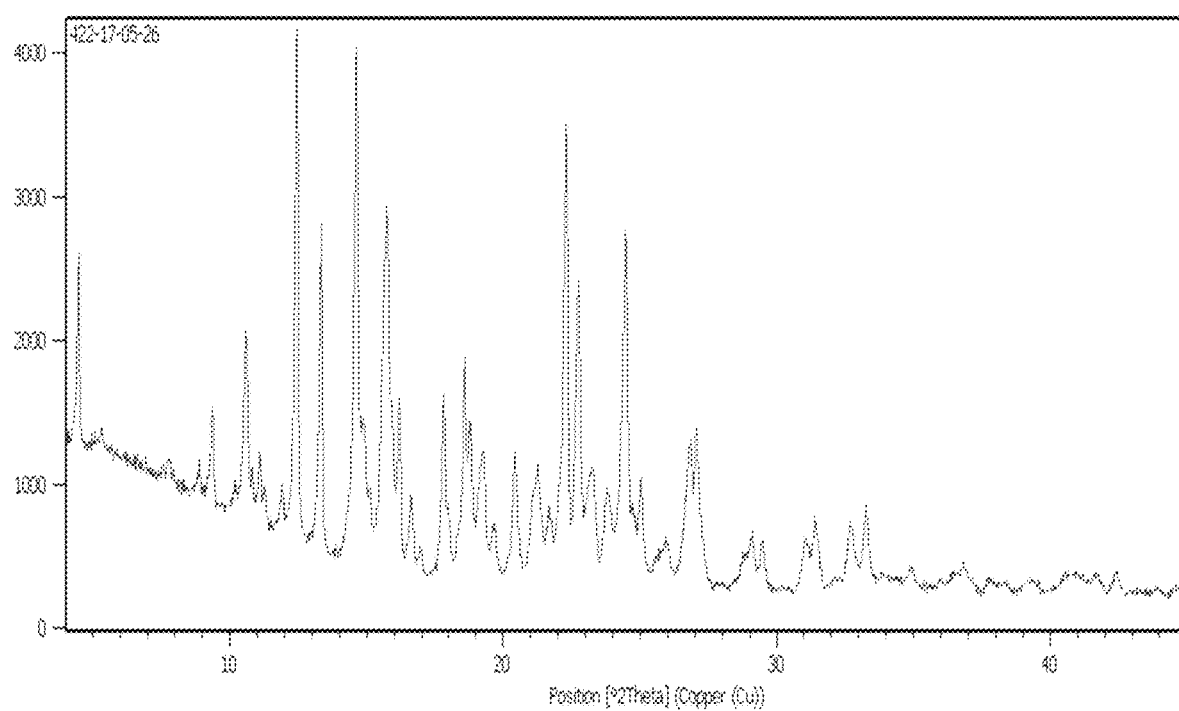
FIG. 3 illustrates an X-ray powder diffractogram of crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

Example 6. X-Ray Powder Diffraction Analysis of Crystalline Form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate An X-ray powder diffractogram (XRPD) of a sample of crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate produced according to Example 3 above was measured using the same instrument and methods described earlier in Example 4. The sample produced the diffractogram pattern illustrated in FIG. 3. The diffractogram peaks from FIG. 3 are shown in Table 3 below.

TABLE 3

| No. | Pos. [°2θ] | Height [cts] | Area [cts.*°2θ] | Rel. Int. [%] | Tip Width | d-spacing [Å] | Derivation |
|---|---|---|---|---|---|---|---|
| 1 | 4.4688 | 2403.67 | 158.65 | 60.40 | 0.0803 | 19.77388 | KA1 + KA2 |
| 2 | 5.1635 | 1091.01 | 432.07 | 27.41 | 0.4818 | 17.11488 | KA1 + KA2 |
| 3 | 7.8056 | 889.39 | 234.82 | 22.35 | 0.3212 | 11.32667 | KA1 + KA2 |
| 4 | 8.8813 | 901.30 | 89.24 | 22.65 | 0.1204 | 9.95701 | KA1 + KA2 |
| 5 | 9.3794 | 1304.02 | 107.59 | 32.77 | 0.1004 | 9.42935 | KA1 + KA2 |
| 6 | 10.6128 | 1816.95 | 209.88 | 45.66 | 0.1105 | 8.33607 | KA1 + KA2 |
| 7 | 10.8175 | 865.62 | 57.14 | 21.75 | 0.0803 | 8.17882 | KA1 + KA2 |
| 8 | 11.1052 | 977.81 | 64.54 | 24.57 | 0.0803 | 7.96759 | KA1 + KA2 |
| 9 | 11.2921 | 729.69 | 72.25 | 18.34 | 0.1204 | 7.83607 | KA1 + KA2 |
| 10 | 11.8994 | 719.74 | 71.26 | 18.09 | 0.1204 | 7.43752 | KA1 + KA2 |
| 11 | 12.4580 | 3979.68 | 328.35 | 100.00 | 0.1004 | 7.10527 | KA1 + KA2 |
| 12 | 13.3436 | 2602.39 | 214.71 | 65.39 | 0.1004 | 6.63560 | KA1 + KA2 |
| 13 | 14.6381 | 3840.47 | 316.86 | 96.50 | 0.1004 | 6.05159 | KA1 + KA2 |
| 14 | 14.9160 | 1218.03 | 100.50 | 30.61 | 0.1004 | 5.93944 | KA1 + KA2 |
| 15 | 15.7565 | 2575.07 | 467.41 | 64.71 | 0.2208 | 5.62447 | KA1 + KA2 |
| 16 | 16.1932 | 1383.44 | 136.97 | 34.76 | 0.1204 | 5.47374 | KA1 + KA2 |

TABLE 3-continued

| No. | Pos. [°2θ] | Height [cts] | Area [cts.*°2θ] | Rel. Int. [%] | Tip Width | d-spacing [Å] | Derivation |
|---|---|---|---|---|---|---|---|
| 17 | 16.6247 | 699.05 | 69.21 | 17.57 | 0.1204 | 5.33264 | KA1 + KA2 |
| 18 | 16.9802 | 306.08 | 40.41 | 7.69 | 0.1606 | 5.22179 | KA1 + KA2 |
| 19 | 17.8146 | 1403.27 | 162.09 | 35.26 | 0.1405 | 4.97904 | KA1 + KA2 |
| 20 | 18.5832 | 1576.48 | 156.08 | 39.61 | 0.1204 | 4.77482 | KA1 + KA2 |
| 21 | 18.8159 | 1168.76 | 115.72 | 29.37 | 0.1204 | 4.71629 | KA1 + KA2 |
| 22 | 19.2940 | 995.45 | 98.56 | 25.01 | 0.1204 | 4.60048 | KA1 + KA2 |
| 23 | 19.6808 | 457.11 | 60.34 | 11.49 | 0.1606 | 4.51093 | KA1 + KA2 |
| 24 | 20.4380 | 999.18 | 164.88 | 25.11 | 0.2007 | 4.34548 | KA1 + KA2 |
| 25 | 21.0640 | 671.96 | 66.53 | 16.88 | 0.1204 | 4.21774 | KA1 + KA2 |
| 26 | 21.2617 | 905.00 | 59.73 | 22.74 | 0.0803 | 4.17896 | KA1 + KA2 |
| 27 | 21.6948 | 596.14 | 78.70 | 14.98 | 0.1606 | 4.09651 | KA1 + KA2 |
| 28 | 22.3013 | 3309.05 | 436.83 | 83.15 | 0.1606 | 3.98645 | KA1 + KA2 |
| 29 | 22.7636 | 2164.57 | 321.46 | 54.39 | 0.1807 | 3.90653 | KA1 + KA2 |
| 30 | 23.2910 | 870.36 | 100.53 | 21.87 | 0.1405 | 3.81925 | KA1 + KA2 |
| 31 | 23.8116 | 713.14 | 82.37 | 17.92 | 0.1405 | 3.73692 | KA1 + KA2 |
| 32 | 24.4828 | 2546.66 | 336.19 | 63.99 | 0.1606 | 3.63596 | KA1 + KA2 |
| 33 | 25.0208 | 776.55 | 64.07 | 19.51 | 0.1004 | 3.55899 | KA1 + KA2 |
| 34 | 25.9952 | 343.93 | 56.75 | 8.64 | 0.2007 | 3.42775 | KA1 + KA2 |
| 35 | 26.8203 | 1058.19 | 139.69 | 26.59 | 0.1606 | 3.32414 | KA1 + KA2 |
| 36 | 27.0532 | 1162.77 | 115.12 | 29.22 | 0.1204 | 3.29605 | KA1 + KA2 |
| 37 | 29.1026 | 401.96 | 53.06 | 10.10 | 0.1606 | 3.06844 | KA1 + KA2 |
| 38 | 29.4926 | 372.62 | 36.89 | 9.36 | 0.1204 | 3.02875 | KA1 + KA2 |
| 39 | 31.0334 | 372.62 | 73.79 | 9.36 | 0.2409 | 2.88180 | KA1 + KA2 |
| 40 | 31.4055 | 526.64 | 52.14 | 13.23 | 0.1204 | 2.84850 | KA1 + KA2 |
| 41 | 32.6975 | 484.50 | 95.94 | 12.17 | 0.2409 | 2.73884 | KA1 + KA2 |
| 42 | 33.2686 | 596.11 | 49.18 | 14.98 | 0.1004 | 2.69311 | KA1 + KA2 |
| 43 | 34.8943 | 169.10 | 33.48 | 4.25 | 0.2409 | 2.57128 | KA1 + KA2 |
| 44 | 36.7921 | 205.78 | 40.75 | 5.17 | 0.2409 | 2.44289 | KA1 + KA2 |
| 45 | 37.7795 | 88.47 | 17.52 | 2.22 | 0.2409 | 2.38129 | KA1 + KA2 |
| 46 | 39.3031 | 75.86 | 40.06 | 1.91 | 0.6424 | 2.29242 | KA1 + KA2 |
| 47 | 40.7277 | 127.40 | 67.27 | 3.20 | 0.6424 | 2.21546 | KA1 + KA2 |
| 48 | 11.6852 | 110.26 | 31.19 | 3.00 | 0.3212 | 2.16676 | KA1 + KA2 |
| 49 | 42.4285 | 135.07 | 26.75 | 3.39 | 0.2409 | 2.13051 | KA1 + KA2 |

Example 7. Differential Scanning Calorimetry (Melting Point) Analysis of Crystalline 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate (Crystalline Form B)

Figure 4:
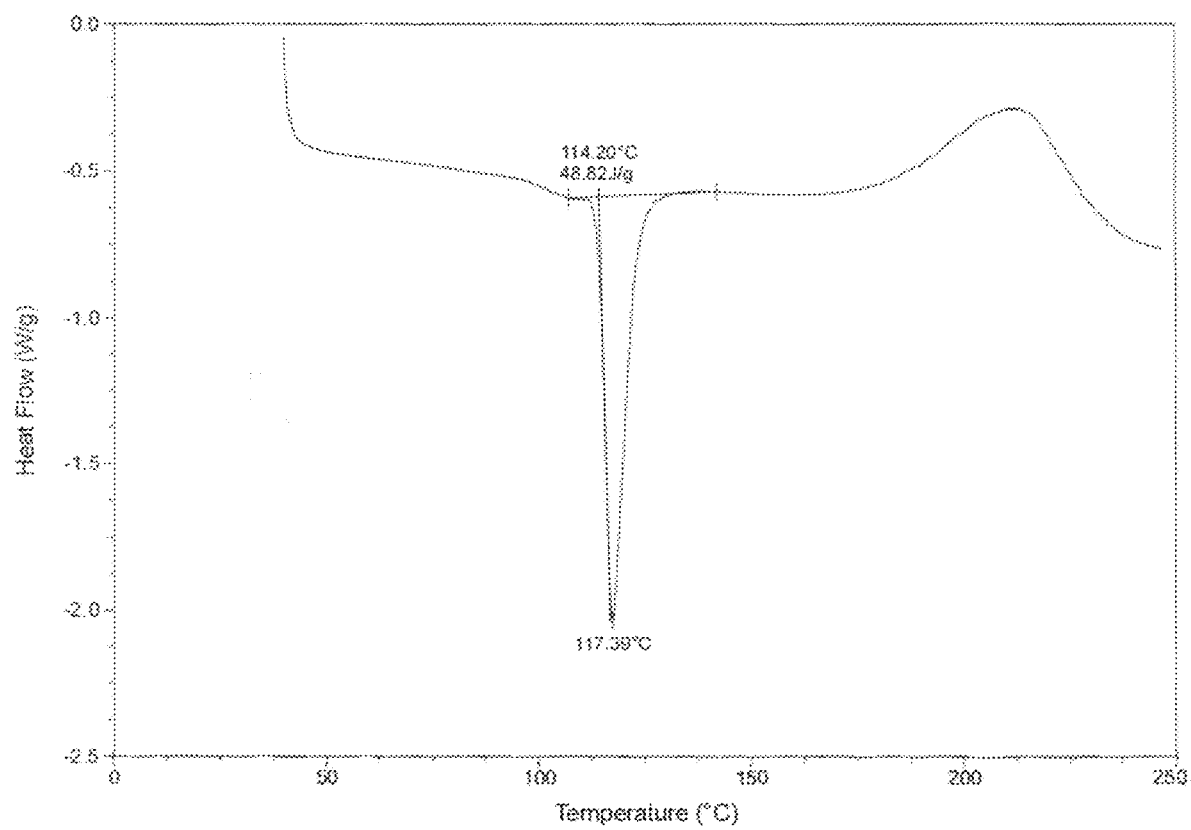
FIG. 4 illustrates a differential scanning calorimetry thermogram of crystalline form B of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate.

Differential scanning calorimetry (DSC) analysis of a crystalline form B sample of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate produced according to Example 3 above was measured using the same method and instrument used in Example 5. The material was run at the appropriate temperature program (Equilibration at Initial Temp, Isothermal, Ramp Rate, Final Temp) to produce the thermogram shown in FIG. 4. DSC analysis shows an endothermic transition with an onset temperature of 114° C. and a ΔH of 48.82 J/g.

Example 8. Immediate Release Oral Dosage Form (Strength 5 mg)

Four different immediate release oral dosage form tablets containing crystalline form A of 2-((R)-3-(1-(1-((R)-1-(2,4-Dichlorophenyl)ethyl)-3-(trifluoromethyl)-1H-pyrazolo[3,4-b]pyrazin-6-yl)azetidin-3-yl)piperidin-1-yl)ethan-1-ol benzene sulfonate (referred to in Examples 8 to 11 as "Compound, crystalline form A" and "drug substance"), corresponding to dosage strengths of 5 mg (Example 8), 25 mg (Example 9), 50 mg (Example 10) and 75 mg (Example 11), were made having the ingredients shown in Tables 3 to 6, respectively. The composition of 5 mg dosage strength oral tablets is shown in Table 4.

TABLE 4

Quantitative Composition of 5 mg Crystalline Form A-Containing Tablets

| Component | Function | 5 mg mg per tablet | (% w/w) |
|---|---|---|---|
| Compound, crystalline form A | Drug substance | 6.45[1] | 10.0 |
| Hydroxy-propyl cellulose | Granulation binder | 1.94 | 3.0 |
| Sodium lauryl sulfate | Wetting Agent | 0.32 | 0.5 |
| Lactose mono-hydrate | Filler | 40.09 | 62.2 |
| Micro-crystalline cellulose | Filler | 13.38 | 20.8 |
| Cros-carmellose sodium | Dis-integrant | 1.94 | 3.0 |
| Magnesium stearate | Lubricant | 0.32 | 0.5 |
| Total Core | | 64.44 | 100.0 |

[1]6.45 mg of the benzene sulfonate salt form corresponds to 5 mg of the free base form.

Granulation:

A high shear wet granulation process was used to manufacture the 5 mg strength tablets in order to improve the content uniformity of the tablet core formulation.

First the drug substance was screened through a 30 mesh screen. Then hydroxypropyl cellulose, sodium lauryl sulfate, lactose monohydrate, microcrystalline cellulose, and cros-carmellose sodium were screened through a 20 mesh screen. These six materials were then high shear granulated in a 25 L bowl with the addition of purified water. Water was added at 350-450 g/min to the granulator operated at an impeller speed of 290 RPM, Chopper speed of 1760. After reaching the end point, the wet granules were delumped in a canonical mill equipped with a 375Q screen. The delumped granules were then dried in oven operated at 40° C. until the amount of water in the granules was less than 4% by weight. The dried granules were then milled in a canonical mill equipped with a 40G or 75R screen.

Lubrication and Compression:

The milled granules were then added to an eight-quart V blender together with magnesium stearate, which was delumped using a 30 mesh screen. These two components were blended for 4 minutes until a uniform blended mixture was reached.

Tablet cores were compressed using a Korsch XL 100 rotary tablet press equipped with 0.2188 inch round toolings. The tablet press was operated at 70 RPM at a compression force of about 10 kN. The tablets had an average weight of 64.2 mg, an average thickness of 1.93 mm and an average hardness of 3.1 kP.

Example 9. Immediate Release Oral Dosage Form (Strength 50 mg)

The composition of 50 mg dosage strength oral tablets is shown in Table 5.

TABLE 5

Quantitative Composition of 50 mg Crystalline Form A-Containing Tablets

| | | 50 mg | |
|---|---|---|---|
| Component | Function | mg per tablet | (% w/w) |
| Compound, crystalline form A | Drug substance | 64.50[1] | 10.0 |
| Hydroxy-propyl cellulose | Granulation binder | 19.40 | 3.0 |
| Sodium lauryl sulfate | Wetting agent | 3.20 | 0.5 |
| Lactose mono-hydrate | Filler | 400.90 | 62.2 |
| Micro-crystalline cellulose | Filler | 133.80 | 20.8 |
| Cros-carmellose sodium | Dis-integrant | 19.40 | 3.0 |
| Magnesium stearate | Lubricant | 3.20 | 0.5 |
| Total Core | | 644.40 | 100.0 |

[1]64.50 mg of the benzene sulfonate salt form corresponds to 50 mg of the free base form.

Granulation:

A similar granulation procedure was followed as described in Example 8.

Lubrication and Compression:

The milled granules were then added to a 16-quart V blender together with magnesium stearate, which was delumped using a 30 mesh screen. These two components were blended for 4 minutes until a uniform blended mixture was reached. Tablet cores were compressed using a Korsch XL 100 rotary tablet press equipped with 0.6496×0.3504 inch caplet toolings. The tablet press was operated at 30 RPM at a compression force of about 29.5 kN. The tablets had an average weight of 647.5 mg, an average thickness of 4.84 mm and an average hardness of 12.3 kP.

Example 10. Immediate Release Oral Dosage Form (Strength 25 mg)

The composition of 25 mg dosage strength oral tablets is shown in Table 6.

TABLE 6

Quantitative Composition of 25 mg Crystalline Form A-Containing Tablets

| | | 25 mg | |
|---|---|---|---|
| Component | Function | mg per tablet | (% w/w) |
| Compound, crystalline form A | Drug substance | 33.07[1] | 20.0 |
| Hydroxy-propyl cellulose | Granulation binder | 4.96 | 3.0 |
| Sodium lauryl sulfate | Wetting agent | 0.83 | 0.5 |
| Lactose mono-hydrate | Filler | 90.53 | 54.75 |
| Micro-crystalline cellulose | Filler | 30.18 | 18.25 |
| Cros-carmellose sodium | Dis-integrant | 4.96 | 3.0 |
| Magnesium stearate | Lubricant | 0.83 | 0.5 |
| Total Core | | 165.36 | 100.0 |
| Opadry amb II | Film Coating agent | 5.00 | 3.0 |
| Total Coated Tablet | | 170.36 | 103.0 |

[1]33.07 mg of the benzene sulfonate salt form corresponds to 25 mg of the free base form.

Granulation and Lubrication:

First, the drug substance was screened through a 30 mesh screen. Then hydroxypropyl cellulose, sodium lauryl sulfate, lactose monohydrate, microcrystalline cellulose, and cros-carmellose sodium were screened through a 20 mesh screen. These six materials were then high shear granulated in a 25 L bowl with the addition of purified water. Water was added at 350-450 g/min to the granulator operated at an impeller speed of 290 RPM, Chopper speed of 1760. After reaching the end point, the wet granules were delumped in a canonical mill equipped with a 375Q screen. The delumped granules were then dried in oven operated at 40° C. until the amount of water in the granules was less than 4% by weight. The dried granules were then milled in a canonical mill equipped with a 75R screen. The milled granules were then added to a one cubic foot V blender together with magnesium stearate, which was delumped using a 30 mesh screen. These two components were blended for 4 minutes until a uniform blended mixture was reached.

Compression:

Tablet cores were compressed using a Korsch XL 100 rotary tablet press equipped with 7.5 mm round toolings. The tablet press was operated at 40 RPM at a compression force of about 15 kN. The tablets had an average weight of 166.4 mg, an average thickness of 3.52 mm and an average hardness of 9.0 kP.

Coating:

Water and Opadry II amb film coating agent were added to a ½ gallon container and blended until a homogeneous suspension was observed. The uncoated tablets were then loaded to a 24-inch Compulab coater equipped with a 15-inch coating pan. The coater was operated at a speed of 12 RPM, a spray rate of 12 g/min and an inlet temperature of 40-60° C. The tablets were sprayed with the suspension until a weight gain of at least 3% was reached. The coated tablets had an average weight of 171.8 mg.

Example 11. Immediate Release Oral Dosage Form (Strength 75 mg)

The composition of 75 mg dosage strength oral tablets is shown in Table 7.

TABLE 7

Quantitative Composition of 75 mg
Crystalline Form A-Containing Tablets

| Component | Function | mg per tablet | (% w/w) |
|---|---|---|---|
| Compound, crystalline form A | Drug substance | 99.20[1] | 20.0 |
| Hydroxy-propyl cellulose | Granulation binder | 14.90 | 3.0 |
| Sodium lauryl sulfate | Wetting agent | 2.50 | 0.5 |
| Lactose mono-hydrate | Filler | 271.60 | 54.75 |
| Micro-crystalline cellulose | Filler | 90.50 | 18.25 |
| Cros-carmellose sodium | Dis-integrant | 14.90 | 3.0 |
| Magnesium stearate | Lubricant | 2.50 | 0.5 |
| Total Core | | 496.00 | 100.00 |

[1]99.20 mg of the benzene sulfonate salt form corresponds to 75 mg of the free base form.

Granulation and Lubrication:

For the granulation and lubrication steps, a similar procedure was followed as described in Example 10.

Compression:

Tablet cores were compressed using a Korsch XL 100 rotary tablet press equipped with 15 mm×7.5 mm caplet toolings. The tablet press was operated at 40 RPM at a compression force of about 9.3 kN. The tablets had an average weight of 494.2 mg, an average thickness of 5.46 mm and an average hardness of 15.2 kP.

It should be noted that there are alternative ways of implementing the present invention. Accordingly, the present embodiments are to be considered as illustrative and not restrictive, and the invention is not to be limited to the details given herein, but may be modified within the scope and equivalents of any claim(s) issuing therefrom. All publications and patents cited herein are incorporated by reference in their entirety.

What is claimed:

1. Compound 2-((R)-3-(1-(1-((R)-1-(2,4-Dichlorophenyl)ethyl)-3-(trifluoromethyl)-1H-pyrazolo[3,4-13]pyrazin-6-yl)azetidin-3-yl)piperidin-1-yl)ethan-1-ol benzene sulfonate in crystalline form.

2. The compound of claim 1, comprising characteristic absorption peaks (2θ) at 18.4°±0.3°, 22.9°±0.3°, 21.2°±0.3°, and 15.9°±0.3° in an X-ray powder diffractogram using Cu Kα radiation.

3. The compound of claim 2, further comprising characteristic absorption peaks (2θ) at 12.2°±0.3°, 23.8°±0.3°, and 25.6°±0.3° in an X-ray powder diffractogram using Cu Kα radiation.

4. The compound of claim 1, further comprising characteristic absorption peaks (2θ) at 23.1°±0.3°, 20.0°±0.3°, and 16.2°±0.3° in an X-ray powder diffractogram using Cu Kα radiation.

5. The compound of claim 1, having an X-ray powder diffractogram using Cu Kα radiation illustrated in FIG. 1.

6. The compound of claim 1, having a melting point between about 170° C. and about 173° C. as determined by differential scanning calorimetry at a scan rate of 5° C./minute.

7. The compound of claim 2, further comprising a characteristic absorption peak (2θ) at 12.2°±0.3° in an X-ray powder diffractogram using Cu Kα radiation.

8. The compound of claim 2, further comprising a characteristic absorption peak (2θ) at 23.8°±0.3° in an X-ray powder diffractogram using Cu Kα radiation.

9. The compound of claim 2, further comprising a characteristic absorption peak (2θ) at 25.6°±0.3° in an X-ray powder diffractogram using Cu Kα radiation.

10. The compound of claim 2, further comprising a characteristic absorption peak (2θ) at 23.1°±0.3° in an X-ray powder diffractogram using Cu Kα radiation.

11. The compound of claim 2, further comprising a characteristic absorption peak (2θ) at 20.0°±0.3° in an X-ray powder diffractogram using Cu Kα radiation.

12. The compound of claim 2, further comprising a characteristic absorption peak (2θ) at 16.2°±0.3° in an X-ray powder diffractogram using Cu Kα radiation.

13. The compound of claim 1, comprising characteristic absorption peaks (2θ) at 12.5°±0.3°, 14.6°±0.3°, 22.3°±0.3°, and 13.3°±0.3° in an X-ray powder diffractogram using Cu Kα radiation.

14. The compound of claim 13, further comprising characteristic absorption peaks (2θ) at 15.8°±0.3°, 24.5°±0.3°, and 4.5°±0.3° in an X-ray powder diffractogram using Cu Kα radiation.

15. The compound of claim 14, further comprising characteristic absorption peaks (2θ) at 22.8°±0.3°, 10.6°±0.3°, and 18.6°±0.3° in an X-ray powder diffractogram using Cu Kα radiation.

16. The compound of claim 13, having an X-ray powder diffractogram using Cu Kα radiation illustrated in FIG. 3.

17. The compound of claim 13, having a melting point between about 116° C. and about 119° C. as determined by differential scanning calorimetry at a scan rate of 5° C./minute.

18. The compound of claim 13, further comprising a characteristic absorption peak (2θ) at 15.8°±0.3° in an X-ray powder diffractogram using Cu Kα radiation.

19. The compound of claim 13, further comprising a characteristic absorption peak (2θ) at 24.5°±0.3° in an X-ray powder diffractogram using Cu Kα radiation.

20. The compound of claim 13, further comprising a characteristic absorption peak (2θ) at 4.5°±0.3° in an X-ray powder diffractogram using Cu Kα radiation.

21. The compound of claim 13, further comprising a characteristic absorption peak (2θ) at 22.8°±0.3° in an X-ray powder diffractogram using Cu Kα radiation.

22. The compound of claim 13, further comprising a characteristic absorption peak (2θ) at 10.6°±0.3° in an X-ray powder diffractogram using Cu Kα radiation.

23. The compound of claim 13, further comprising a characteristic absorption peak (2θ) at 18.6°±0.3° in an X-ray powder diffractogram using Cu Kα radiation.

24. A pharmaceutical composition comprising the crystalline compound of claim 1 and a pharmaceutically acceptable vehicle.

25. A pharmaceutical composition comprising the crystalline compound of claim 2 and a pharmaceutically acceptable vehicle.

26. A pharmaceutical composition comprising the crystalline compound of claim 13 and a pharmaceutically acceptable vehicle.

27. The pharmaceutical composition of claim 24, wherein the composition is an oral tablet dosage form.

28. The pharmaceutical composition of claim 27, wherein the composition comprises 75 mg of the crystalline compound.

29. The pharmaceutical composition of claim 27, wherein the composition comprises 25 mg of the crystalline compound.

30. The pharmaceutical composition of claim 24, wherein the composition comprises a wetting agent.

31. The pharmaceutical composition of claim 30, wherein the wetting agent is sodium lauryl sulfate.

32. The pharmaceutical composition of claim 24, wherein the composition comprises a water soluble excipient.

33. The pharmaceutical composition of claim 32, wherein the water soluble excipient is lactose mono-hydrate.

34. The pharmaceutical composition of claim 32, wherein the water soluble excipient is at least 50% by weight of said pharmaceutical composition.

35. The pharmaceutical composition of claim 24, wherein the composition comprises a disintegrant.

36. The pharmaceutical composition of claim 35, wherein the disintegrant is cros-carmellose sodium.

37. A method of treating an immune-, inflammatory-, or cancer-related disease or disorder, comprising administering to a patient in need of such treatment the crystalline compound of claim 1.

38. A method of treating an immune-, inflammatory-, or cancer-related disease or disorder, comprising administering to a patient in need of such treatment the pharmaceutical composition of claim 24.

39. The method of claim 37, wherein the disease or disorder is selected from allergy-related disorders, hypersensitivity, anaphylactic responses, gastrointestinal disorders, respiratory allergic diseases, hypersensitivity lung diseases, autoimmune diseases, inflammatory dermatoses, graft rejection, allograft rejection, transplant rejection, cancer, metastatic cancer, and neurodegenerative disease.

40. The method of claim 37, wherein the disease or disorder is selected from inflammatory bowel disease, Crohn's disease, ulcerative colitis, ileitis, enteritis, psoriasis, dermatitis, eczema, atopic dermatitis, allergic contact dermatitis, dermatomyositis, urticaria, pruritus, vasculitis, scleroderma, asthma, COPD, allergic rhinitis, rheumatoid arthritis, psoriatic arthritis, multiple sclerosis, systemic lupus erythematosus, type I diabetes, glomerulonephritis, leukemia, lymphoma, gastric cancer, atherosclerosis, Alzheimer's disease, encephalitis, meningitis, hepatitis, nephritis, sepsis, sarcoidosis, allergic conjunctivitis, otitis, and sinusitis, idiopathic pulmonary fibrosis, contact dermatitis, pulmonary fibrosis, hepatic inflammation, asthma, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, nasopharangeal carcinoma, Hodgkin lymphoma, breast invasive carcinoma, lung adenocarcinoma, lung squamous cell carcinoma and granuloma development.

41. The method of claim 37, wherein the crystalline compound is co-administered with another therapeutic agent.

42. The method of claim 41, wherein the another therapeutic agent is pembrolizumab.

43. The method of claim 38, wherein the disease or disorder is selected from allergy-related disorders, hypersensitivity, anaphylactic responses, gastrointestinal disorders, respiratory allergic diseases, hypersensitivity lung diseases, autoimmune diseases, inflammatory dermatoses, graft rejection, allograft rejection, transplant rejection, cancer, metastatic cancer, and neurodegenerative disease.

44. The method of claim 38, wherein the disease or disorder is selected from inflammatory bowel disease, Crohn's disease, ulcerative colitis, ileitis, enteritis, psoriasis, dermatitis, eczema, atopic dermatitis, allergic contact dermatitis, dermatomyositis, urticaria, pruritus, vasculitis, scleroderma, asthma, COPD, allergic rhinitis, rheumatoid arthritis, psoriatic arthritis, multiple sclerosis, systemic lupus erythematosus, type I diabetes, glomerulonephritis, leukemia, lymphoma, gastric cancer, atherosclerosis, Alzheimer's disease, encephalitis, meningitis, hepatitis, nephritis, sepsis, sarcoidosis, allergic conjunctivitis, otitis, and sinusitis, idiopathic pulmonary fibrosis, contact dermatitis, pulmonary fibrosis, hepatic inflammation, asthma, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, nasopharangeal carcinoma, Hodgkin lymphoma, breast invasive carcinoma, lung adenocarcinoma, lung squamous cell carcinoma and granuloma development.

45. The method of claim 38, wherein the crystalline compound is co-administered with another therapeutic agent.

46. The method of claim 45, wherein the another therapeutic agent is pembrolizumab.

* * * * *